(12) United States Patent
Pudelko et al.

(10) Patent No.: US 7,588,555 B2
(45) Date of Patent: Sep. 15, 2009

(54) BI-DIRECTIONAL CATHETER ASSEMBLY AND METHOD THEREFOR

(75) Inventors: Greg Pudelko, Rosesville, MN (US); Brian Fischer, Minneapolis, MN (US); Brian Honebrink, Stillwater, MN (US)

(73) Assignee: Enpath Medical, Inc., Minneapolis, MN (US)

( * ) Notice: Subject to any disclaimer, the term of this patent is extended or adjusted under 35 U.S.C. 154(b) by 577 days.

(21) Appl. No.: 10/670,150

(22) Filed: Sep. 24, 2003

(65) Prior Publication Data

US 2005/0065467 A1    Mar. 24, 2005

(51) Int. Cl.
*A61M 37/00* (2006.01)
(52) U.S. Cl. ................................. 604/95.04; 604/528
(58) Field of Classification Search ............. 604/510, 604/93.01, 535, 523, 524, 526, 528, 534, 604/95.04
See application file for complete search history.

(56) References Cited

U.S. PATENT DOCUMENTS

| | | | |
|---|---|---|---|
| 4,898,577 A | 2/1990 | Badger et al. ............ 604/53 |
| 5,195,968 A | * 3/1993 | Lundquist et al. ....... 604/95.04 |
| 5,358,478 A | 10/1994 | Thompson et al. |
| 5,545,200 A | 8/1996 | West et al. ............. 607/122 |
| 5,588,964 A | * 12/1996 | Imran et al. ........... 604/95.04 |
| 5,642,736 A | 7/1997 | Avitall |
| 5,656,030 A | * 8/1997 | Hunjan et al. .......... 604/95.01 |
| 5,807,249 A | * 9/1998 | Qin et al. ................ 600/374 |
| 5,826,576 A | 10/1998 | West ...................... 128/642 |
| 5,897,554 A | 4/1999 | Chia et al. ............... 606/41 |
| 5,944,690 A | 8/1999 | Falwell et al. ........... 604/95 |
| 6,171,277 B1 | 1/2001 | Ponzi ..................... 604/95.04 |
| 6,183,463 B1 | 2/2001 | Webster, Jr. ............. 604/528 |
| 2003/0050598 A1 | * 3/2003 | Hayzelden .............. 604/95.04 |

FOREIGN PATENT DOCUMENTS

| | | |
|---|---|---|
| EP | 1038545 A2 | 9/2000 |
| EP | 1205208 A1 | 5/2002 |
| WO | WO-2005/030312 A1 | 4/2005 |

OTHER PUBLICATIONS

"International Search Report for correspoonding PCT Application No. PCT/US2004/031431", (Feb. 21, 2005),4 pgs.
"Canadian Application Serial No. 2554549, Office Action mailed Aug. 11, 2008", 2 pgs.
"International Application Serial No. PCT/US2004/031431, International Preliminary Report on Patentability mailed Apr. 6, 2006", 10 pgs.
"International Application Serial No. PCT/US2004/031431, International Search Report mailed Feb. 21, 2005", 7 pgs.
"International Application Serial No. PCT/US2004/031431, Written Opinion mailed Feb. 21, 2005", 8 pgs.

* cited by examiner

*Primary Examiner*—Nicholas D Lucchesi
*Assistant Examiner*—Laura A Bouchelle
(74) *Attorney, Agent, or Firm*—Schwegman, Lundberg & Woessner, P.A.

(57) ABSTRACT

A catheter assembly includes a catheter body and housing attached to the catheter body proximal end, where an actuator lumen extends through the catheter body. A flexible element extends from an actuator member within the housing through the actuator lumen to a deflectable distal end. A first tubular support is provided that is coupled to the flexible element. A second tubular support is coupled with the first tubular support and slidably coupled to the flexible element. In one option, the first tubular support and second tubular support constrain lateral movement of the flexible element when the catheter assembly is operated.

35 Claims, 12 Drawing Sheets

BI-DIRECTIONAL CATHETER ASSEMBLY AND METHOD THEREFOR

TECHNICAL FIELD

The present invention relates generally to a deflectable catheter assembly. More particularly, it pertains to a bi-directional catheter assembly for a deflectable catheter assembly.

BACKGROUND

Increase in the use of stents, leads, and ablation techniques in branch vessels has provided an increased demand on the placement techniques for these devices. For some procedures, it is necessary to initially position a guidewire into a desired part of the lumen of a desired vessel or duct, such as a blood vessel. After the guidewire is positioned within the desired location, a catheter or other tubular device may be positioned over the guidewire and used to convey other medical instruments into the desired blood vessel or duct.

Alternatively, a guiding catheter is used to negotiate the vasculature of a patient. One example of a guiding catheter is described in U.S. Pat. No. 4,898,577 to Badger et al. The Badger guiding catheter includes a single elongate shaft that has a deflectable distal portion controllable by a pull wire. For bi-directional catheters, multiple pull wires are used to pull on the distal end and cause it to defect in more than one direction. One example of such a catheter is shown in U.S. Pat. No. 6,171,277. While bi-directional catheters are helpful, for example, in traversing a complex vasculature, conventional catheters are bulky and have a relatively large outer diameter given the use of multiple pull wires, or the size of the pull wires.

Accordingly, what is needed is a deflectable catheter that overcomes the shortcomings of previous bi-directional catheters. What is further needed is a catheter that allows for more accurate positioning of the distal end of the deflectable catheter, in a less traumatic way.

SUMMARY

A deflectable catheter assembly includes a catheter body and a housing coupled to a proximal end of the catheter body. A flexible element extends through the housing and an actuator lumen within the catheter body to a deflectable distal end. The deflectable distal end is controllable by the flexible element. A support assembly including a first tubular support is coupled to the flexible element and coupled to an actuator mechanism disposed within the housing.

Several options for the deflectable catheter assembly follow. For example, in one option, a second tubular support is telescopically coupled with the first tubular support and coupled to a surface defining the actuator lumen. In another option, an inner surface of the second tubular support is dimensioned and configured to snugly envelop and slidably couple with the flexible element. In yet another option, the outer surface of the first tubular support has a complementary perimeter dimensioned and configured to slidably couple with the surface defining the actuator lumen. The surface defining the actuator lumen has a circular geometry, in one option. In still another option, a first tubular support intermediate surface and second tubular support intermediate surface slidably couple the first tubular support with the second tubular support.

In another embodiment, a method comprises manipulating a deflectable catheter assembly into a first orientation, the catheter assembly includes a catheter body and a housing coupled to a proximal end of the catheter body. An actuator lumen extends through the catheter body, and a flexible element extends from an actuator member coupled with the housing to a deflectable distal end. A first tubular support is coupled to the flexible element and coupled to the actuator member. A second tubular member is coupled to a surface defining the actuator lumen and coupled to the flexible element. The method further includes constraining lateral movement of the flexible element, including bracing the flexible element with the first tubular support and second tubular support. Additionally, the method includes further manipulating the actuator member to actuate the flexible element and thereby deflect the deflectable distal end into a disparate orientation.

Several options for the method follow. In one option, the first tubular support and actuator member are telescopically advanced with respect to the second tubular support. In another option, further manipulating the actuator member to deflect the deflectable distal end into a disparate orientation includes constraining lateral movement of the flexible element within the actuator lumen with the first tubular support and second tubular support.

In yet another embodiment, a method comprises manipulating a deflectable catheter assembly into a first orientation, the catheter assembly includes a catheter body and housing coupled to the proximal end of the catheter body. An actuator lumen extends through the catheter body, and a flexible element extends within the actuator lumen. The flexible element extends from an actuator member coupled with the housing to a deflectable distal end. A first tubular support is coupled to the flexible element and coupled to the actuator member. A second tubular support is coupled to a surface defining the actuator lumen and slidably coupled to the flexible element. The method further includes, longitudinally advancing the flexible element and first tubular support along the longitudinal axis of the actuator lumen. The second tubular support is stationary with respect to the housing. The first tubular support and second tubular support remain aligned with the actuator lumen longitudinal axis. Additionally, the method includes further manipulating the actuator member to advance the flexible element and deflect the deflectable distal end into a disparate orientation.

Several options for the method follow. In one option, the first tubular support and actuator member are telescopically advanced with respect to the second tubular support. In another option, the method further includes constraining lateral movement of the flexible element including bracing the flexible element with the first tubular support and second tubular support. In yet another option, further manipulating the actuator member to deflect the deflectable distal end into a disparate orientation includes constraining lateral movement of the flexible element within the actuator lumen with the first tubular support and second tubular support. Additionally, another option for further manipulating the actuator member includes longitudinally advancing the flexible element and first tubular support along the longitudinal axis of the actuator lumen, while the second tubular support is stationary with respect to the housing, and the first tubular support and second tubular support remain aligned with the actuator lumen longitudinal axis.

The deflectable catheter allows for bi-directional deflection of the catheter body using a single pull wire having a smaller diameter than what is otherwise required. The tubular supports brace the narrow pull wire when compressed to prevent buckling due to articulation of the catheter into a disparate orientation from that caused by tensioning. Consequently, the pull wire and support assembly require significantly less volume within the catheter and leave additional space for the delivery lumen while allowing bi-directional deflection of the catheter.

Furthermore, the telescopic movement of one support member with respect to another allows bracing of the pull wire under any deflection of the catheter caused by compression. Consequently, any desired bi-directional deflection of the catheter is available where the support assembly is used with the narrow pull wire.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the subject matter of this application is defined by the appended claims and their equivalents.

Figures 1A, 1B:
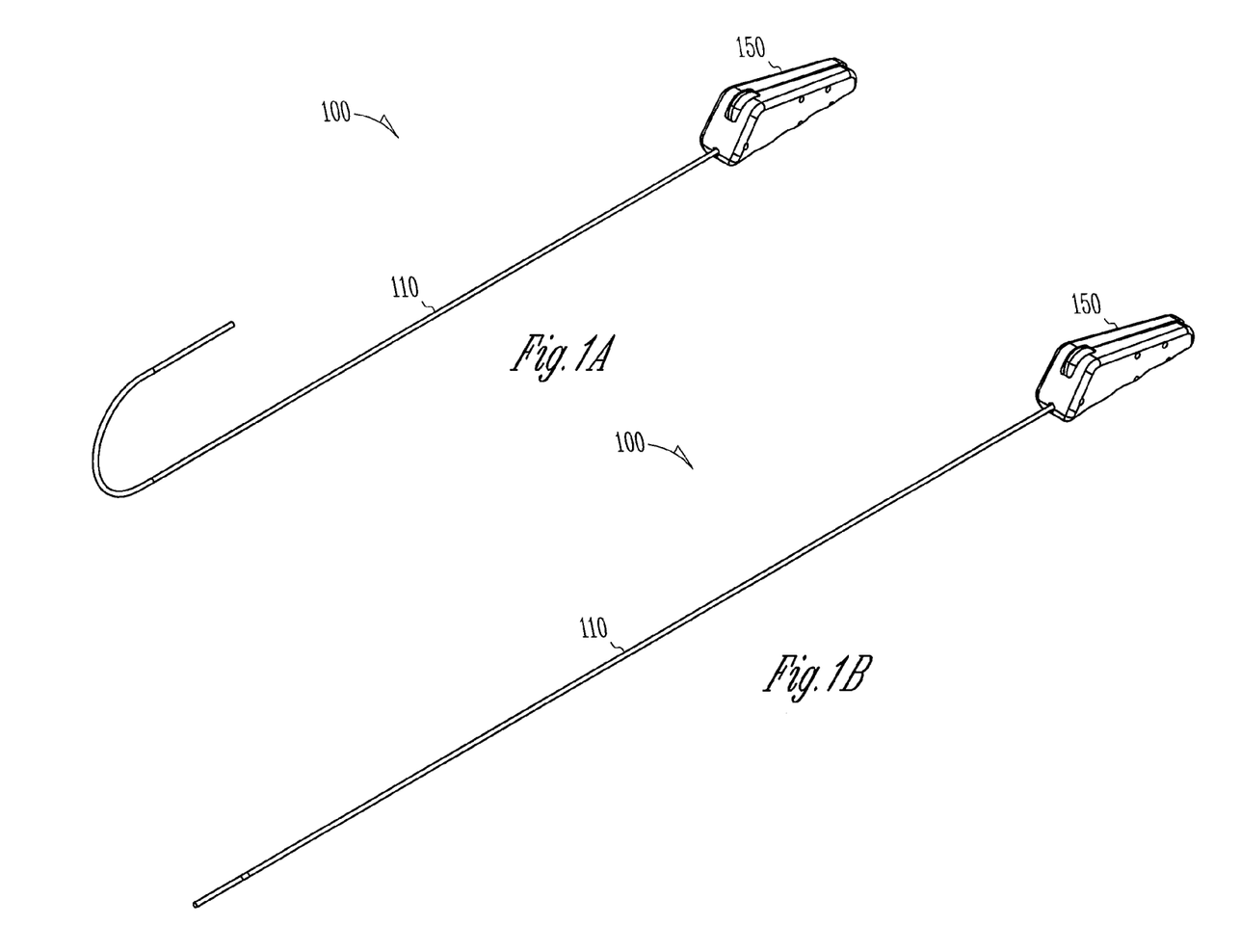
FIG. 1A is a perspective view illustrating a deflectable catheter assembly constructed in accordance with one embodiment.
FIG. 1B is a perspective view illustrating a deflectable catheter assembly constructed in accordance with one embodiment.
Figure 1C:
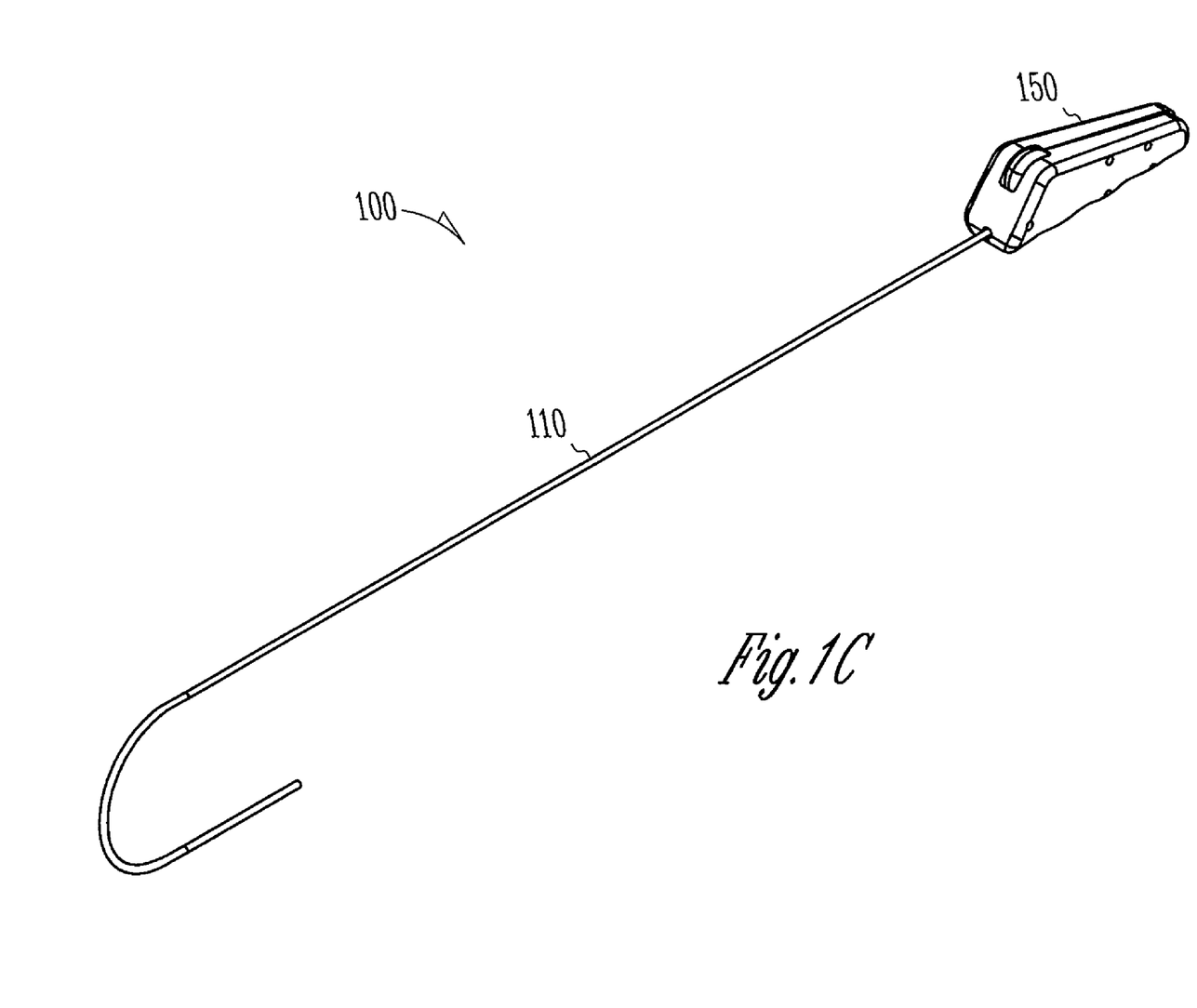
FIG. 1C is a perspective view illustrating a deflectable catheter assembly constructed in accordance with one embodiment.
Figure 2:
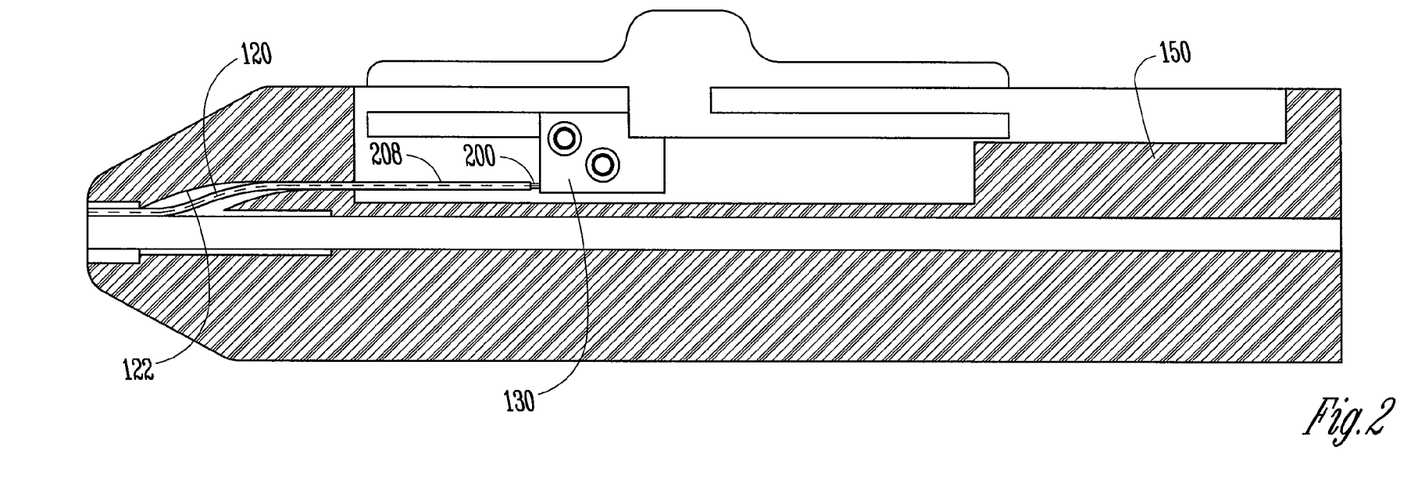
FIG. 2 is a cross-sectional view illustrating a portion of the deflectable catheter assembly constructed in accordance with one embodiment.
Figure 3:
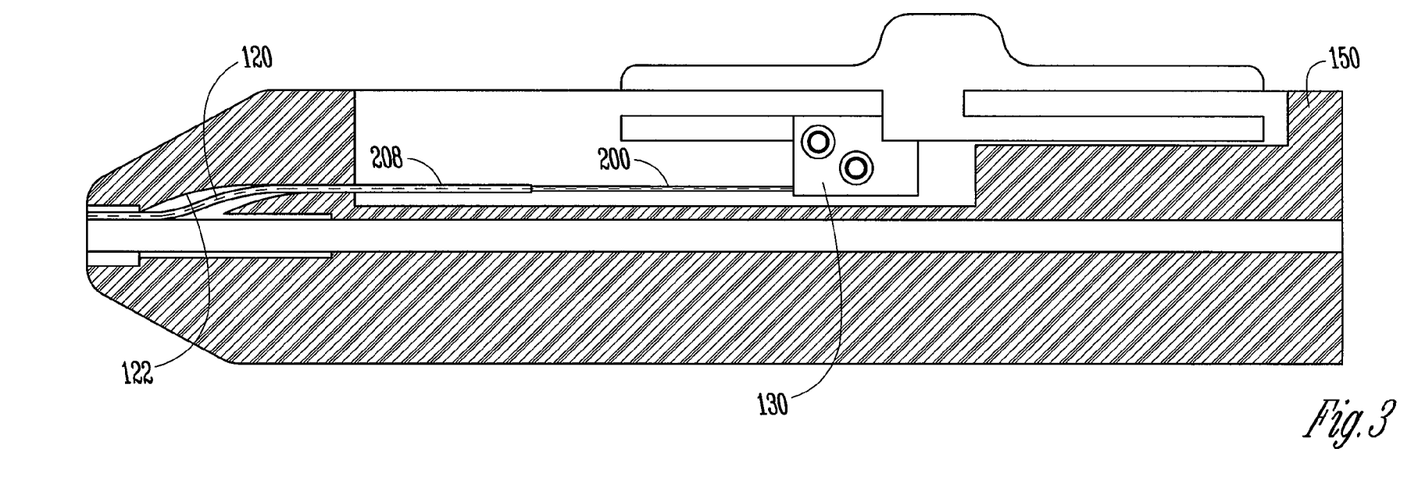
FIG. 3 is a cross-sectional view illustrating a portion of the deflectable catheter assembly constructed in accordance with one embodiment.

FIGS. 1A, 1B and 1C illustrate a deflectable catheter assembly 100, where FIG. 1A illustrates the deflectable catheter assembly 100 in one articulated position, and FIG. 1C illustrates the catheter assembly 100 in another articulated orientation. FIG. 1B illustrates the deflectable catheter assembly 100 in an unarticulated position. The deflectable catheter assembly 100 includes a catheter body 110 and a handle assembly 150 that houses steering mechanisms for deflection of the catheter body 110. The handle assembly 150 allows for the selectable deflection of a distal end of the catheter body 110 into any number of disparate orientations. One example of the handle assembly 150 is described in co-pending application Ser. No. 10/179,633, assigned to MedAmicus, Inc., and is entitled "Articulating Handle For a Deflectable Catheter," which is incorporated herein by reference. FIGS. 2 and 3 illustrate one option where a flexible element, such as a pull wire 120, is connected to an actuator mechanism 130 that is slid or rotated to apply tension or compression to the pull wire 120. As shown in FIGS. 1A and 1C, when tension or compression is applied to the pull wire 120, the pull wire anchor (described below) at the distal end of the catheter body 110 is pulled or pushed causing the distal portion of the catheter body 110 to curve in predetermined directions.

Figures 4, 5:
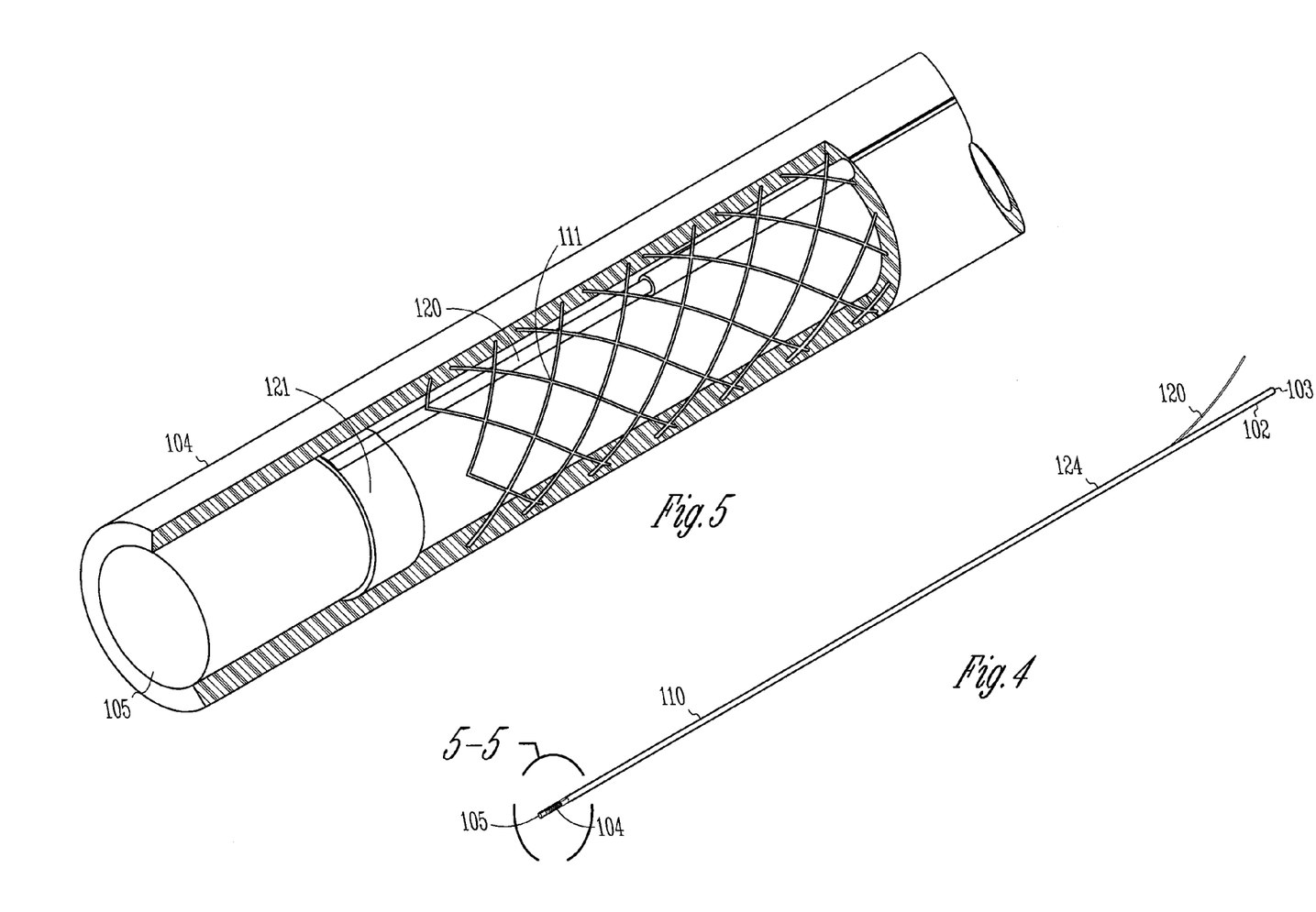
FIG. 4 is a perspective view illustrating a deflectable catheter body constructed in accordance with one embodiment.
FIG. 5 is a perspective view illustrating a distal portion of the deflectable catheter body constructed in accordance with one embodiment.

With reference to FIG. 4, the catheter body 110 comprises an elongate tubular construction that is flexible yet substantially non-compressible along its length. The deflectable catheter body 110 extends from a proximal end 102 to a deflectable distal end 104, where the deflectable distal end 104 is adapted to be disposed within a patient. At the proximal end 102 is a proximal tip 103, and at the distal end 104 is a distal tip 105. At the proximal end 102, the physician controls the deflection of the deflectable catheter body 110 with the handle assembly 150 (FIGS. 1A, 1B, 1C, 2 and 3) containing the actuator mechanism 130 (FIGS. 2 and 3) and a pull wire 120 (FIGS. 2 and 3), as further described below. The distal end 104 is deflected to traverse various branch vessels with the catheter assembly 100 (FIGS. 1A and 1C).

FIG. 5 illustrates a partial cut-away view of FIG. 4, including the distal end 104 of the catheter body 110. The catheter body 110 includes a pull wire anchor 121 that is secured to the catheter body 110. The pull wire 120 is secured to the pull wire anchor 121. It should be noted that the pull wire 120 can be secured to the distal end 104 of the catheter body 110 by other means. In one option, the catheter body 110 includes a stiffening member embedded therein, such as a braided stainless steel member 111. The stiffening member facilitates rotation of the distal end 104 from the proximal end 102, and also assists in preventing the catheter body 110 from collapsing.

Figure 6:
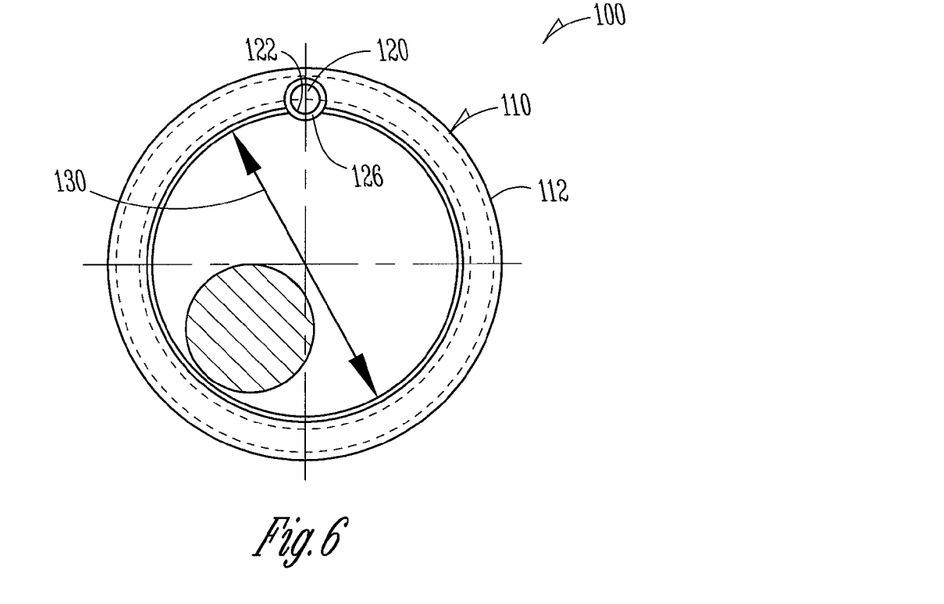
FIG. 6 is an end view of the distal end of the deflectable catheter assembly constructed in accordance with one embodiment.
Figure 7:
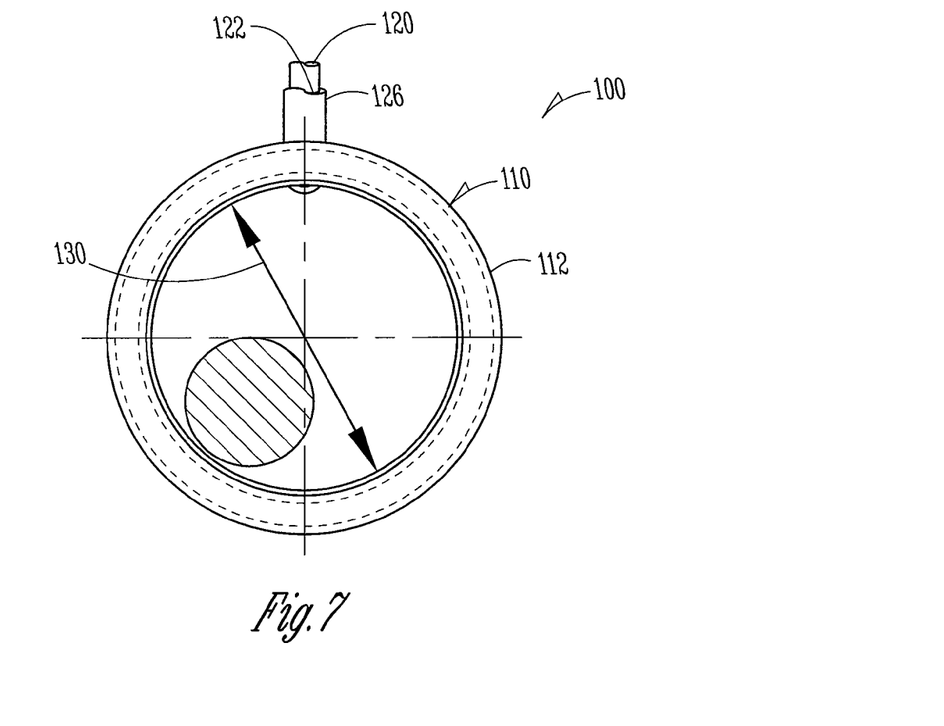
FIG. 7 is a front view of the proximal end of the deflectable catheter assembly constructed in accordance with one embodiment.

As shown in FIGS. 6 and 7 the pull wire 120 is received within an actuator lumen 122. The actuator lumen 122 is disposed within the catheter body 110 and handle assembly 150 (see FIGS. 2 and 3). The pull wire 120 is movably disposed within the actuator lumen 122. In one example, the actuator lumen 122 extends from a location near or at the distal end 104 (see FIG. 5) to an intermediate location that does not extend through the proximal end 102 (see FIG. 4). For example, as shown in FIG. 4, when the pull wire 120 exits the catheter body 110 near the proximal end 102 the actuator lumen 122 consequently exits at a location in a side wall 124 of the catheter body 110. FIG. 7 illustrates an end view of the catheter body 110 at the proximal end 102. The lumen 122 does not extend to the proximal end 102 nor to the proximal tip 103 of the catheter body 110. Therefore, there is no cross-contamination of fluids or gasses from a delivery lumen to the actuator lumen 122, or vice versa. As shown in FIGS. 2 and 3, in another example, the actuator lumen 122 extends through the proximal end 102 (see FIG. 4) and into the handle assembly 150 (see FIGS. 2 and 3).

Figures 8, 9:
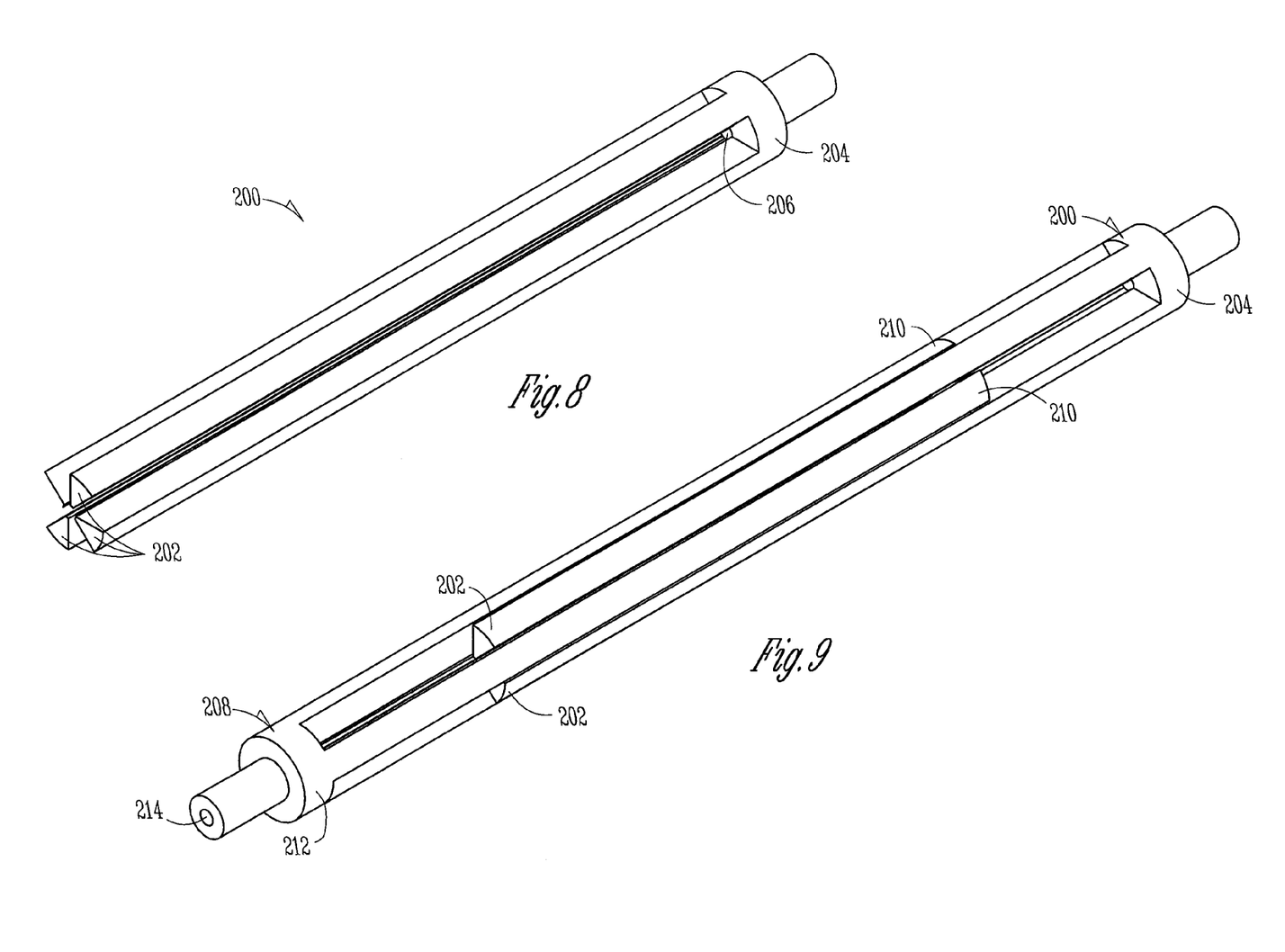
FIG. 8 is a perspective view illustrating a tubular support member constructed in accordance with one embodiment.
FIG. 9 is a perspective view illustrating tubular support members telescopically engaged in accordance with one embodiment.
Figure 16:
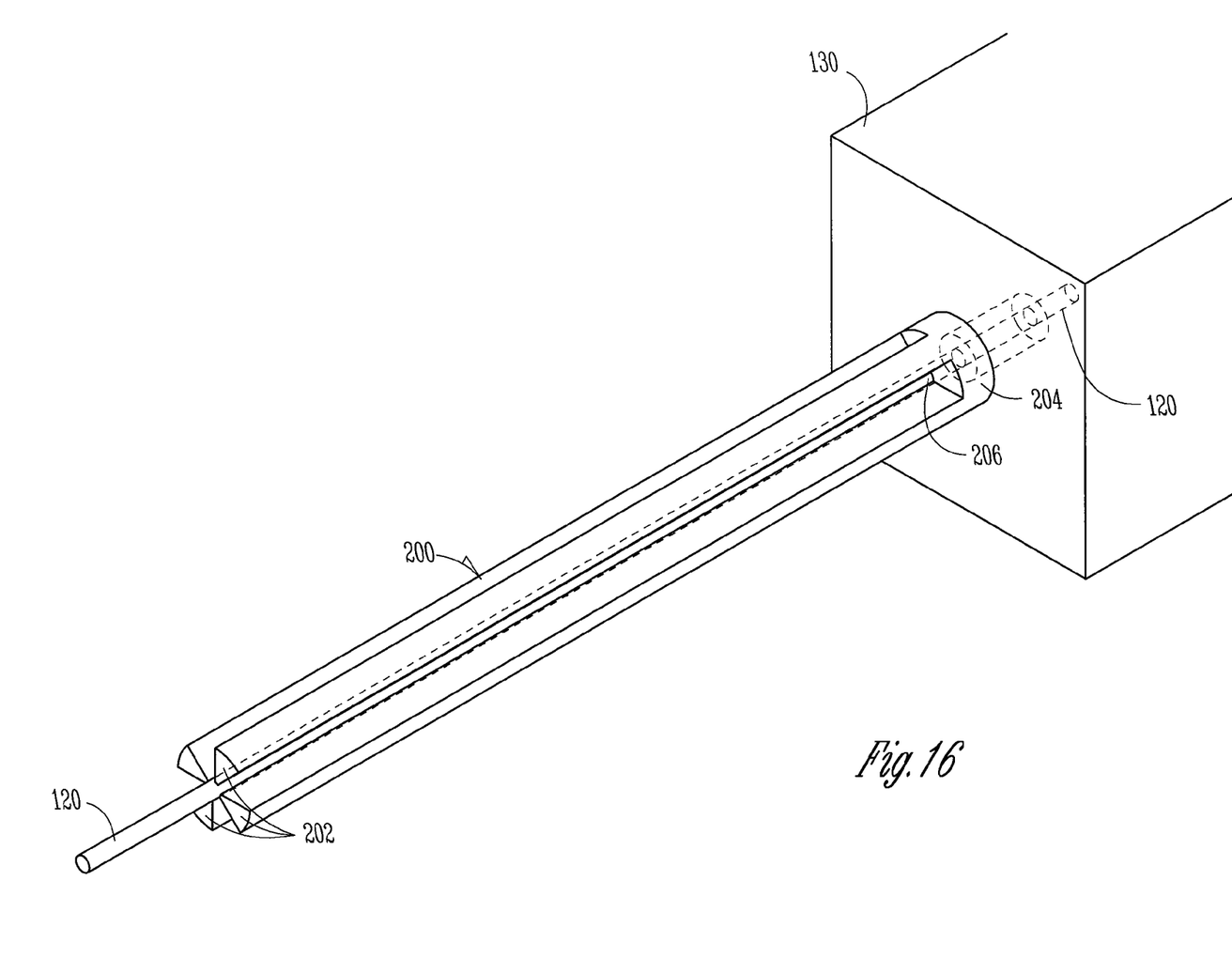
FIG. 16 is a perspective view illustrating a tubular support member engaged in accordance with one embodiment.

The following is one example of how to construct the pull wire support assembly. It should be noted that several variations exist, including, for example, interposed telescoping members. With reference to FIG. 8, in one option a first tubular support member 200 is shown that is aligned along the longitudinal axis of the actuator lumen 122. The first tubular support member 200 presents one or more fingers 202 that extend from a base 204 parallel to a longitudinal axis of the member 200. As shown in FIG. 16, in one option, the first tubular support member 200 is coupled with the pull wire 120 and fixedly coupled with the actuator mechanism 130. In another option, the first tubular support member 200 is fixedly coupled to the pull wire 120. In yet another option, the first tubular support member 200 is fixedly coupled to both the pull wire 120 and actuator mechanism 130. In one example, the first tubular support member 200 extends from a proximal end adjacent the actuator mechanism 130 to a distal end within actuator lumen 122. The distal end of the first tubular support member 200 is selectively positioned (described below) between the actuator mechanism 130 and the exit point (described above) of the pull wire 120 from catheter body 110.

Figure 12:
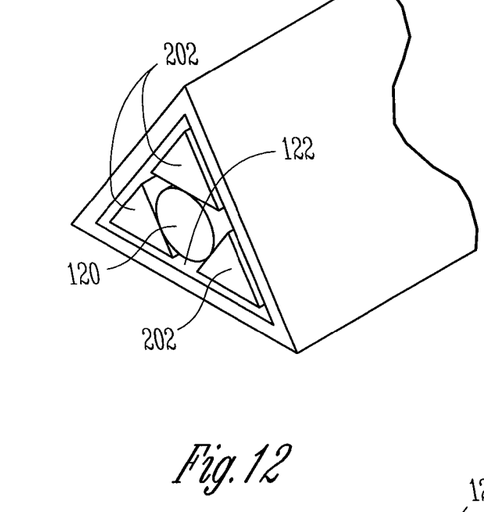
FIG. 12 is a front view illustrating a tubular support member telescopically engaged in accordance with one embodiment.
Figure 13:
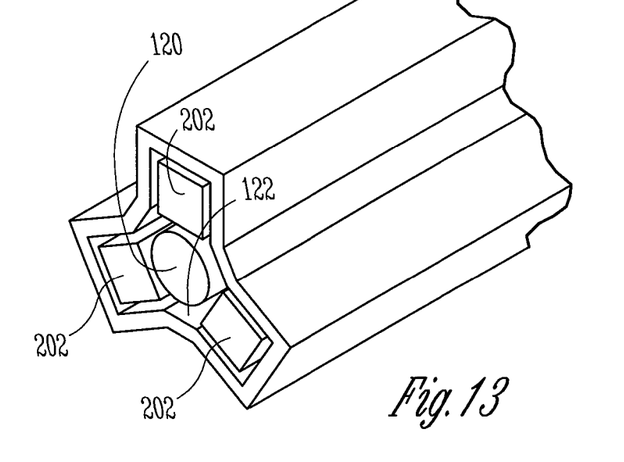
FIG. 13 is a front view illustrating a tubular support member telescopically engaged in accordance with one embodiment.
Figure 14:
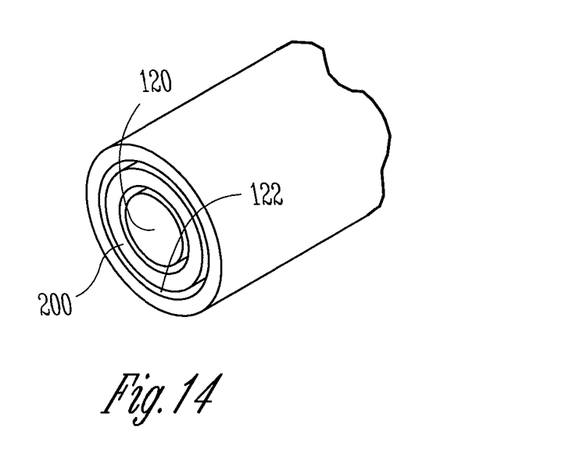
FIG. 14 is a front view illustrating a tubular support member telescopically engaged in accordance with one embodiment.

Several means exist for snugly coupling the first tubular support member 200 with the surface defining the actuator lumen 122. In the following options the outer surfaces of the fingers 202 and base 204 define a perimeter dimensioned and configured to enable the first tubular support member 200 to be housed within the actuator lumen 122. In one option, the outer surfaces of the fingers 202 and base 204 are dimensioned and configured to be coupled within an actuator lumen 122 having a circular cross-section. The fingers 202 and base 204 have a substantially circular outer geometry so as to complement the circular actuator lumen 122. In another option, shown in FIG. 12, the actuator lumen 122 has a triangular cross-section geometry. The outer surfaces of the fingers 202 and base 204 have a complementary triangular geometry so as to be snugly coupled within the triangular actuator lumen 122. In yet another option, shown in FIG. 13, the actuator lumen 122 has a cross-section geometry resembling an inverted 'Y' or three pointed star. Each 'point' of the actuator lumen 122 has a square furrow. The outer surfaces of the fingers 202 and base 204 have a complementary square geometry so as to be snugly coupled within the actuator lumen 122. In still another option, shown in FIG. 14, the first tubular support member 200 is a cylindrical member without fingers.

Figure 17:
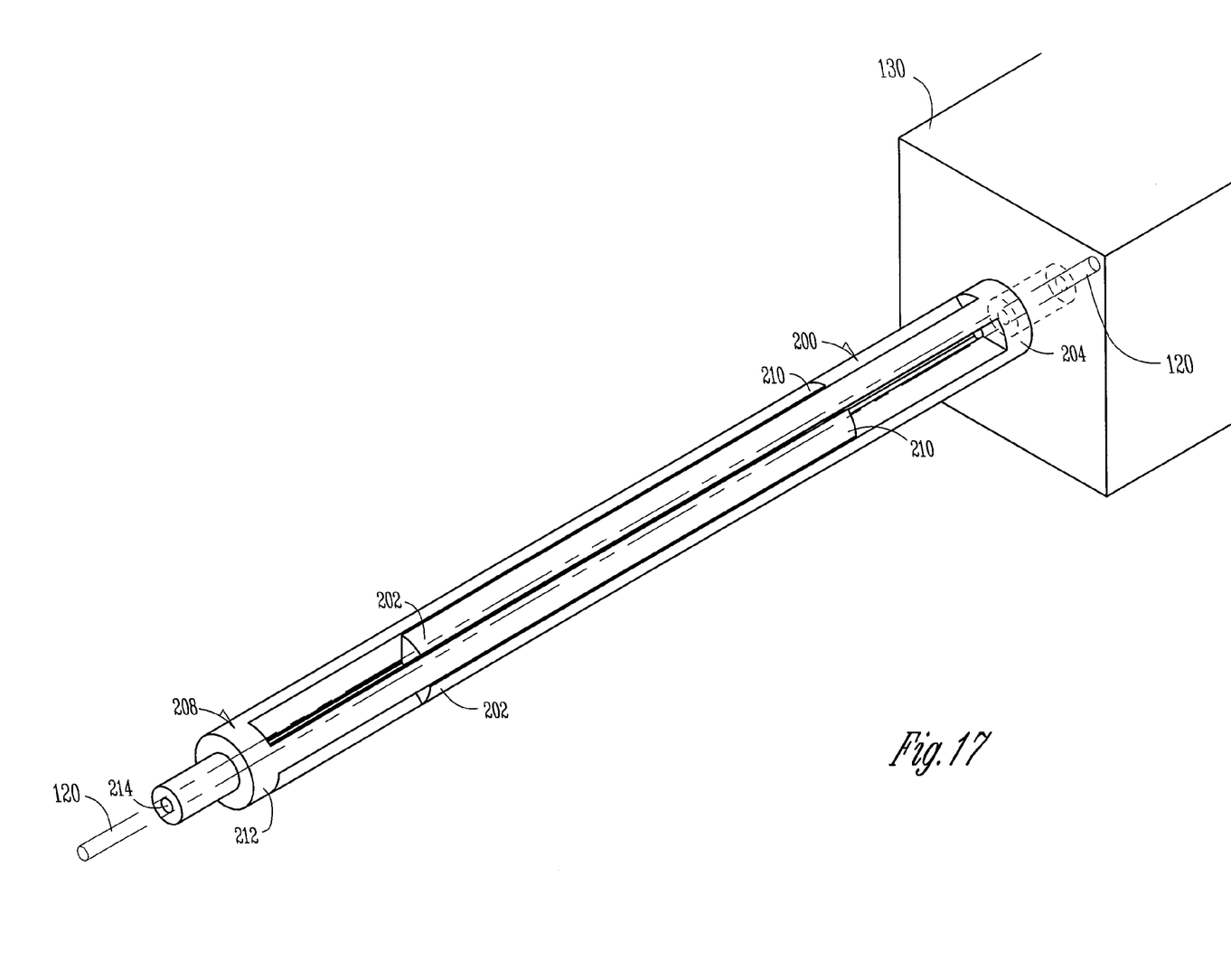
FIG. 17 is a perspective view illustrating tubular support members telescopically engaged in accordance with one embodiment.

Referring again to FIG. 8, where the first tubular support member 200 presents fingers 202, a pull wire lumen 206 is provided about the longitudinal axis of the first tubular support member 200 and extends through the base 204. The inner surfaces of the fingers 202 further define the pull wire lumen 206. As shown in FIGS. 16 and 17, in one option, the pull wire 120 is coupled to the inner surfaces of the fingers 202 and the base 204 within the pull wire lumen 206. The first tubular support member 200 is dimensioned and configured to restrain the pull wire 120 from moving laterally with respect to the longitudinal axis of the first tubular support member 200. In one example, the diameter of the pull wire 120 is only substantially similar or slightly smaller than the diameter of the pull wire lumen 206, and thus the first tubular support member 200 prevents lateral movement of the pull wire 120.

Figure 10:
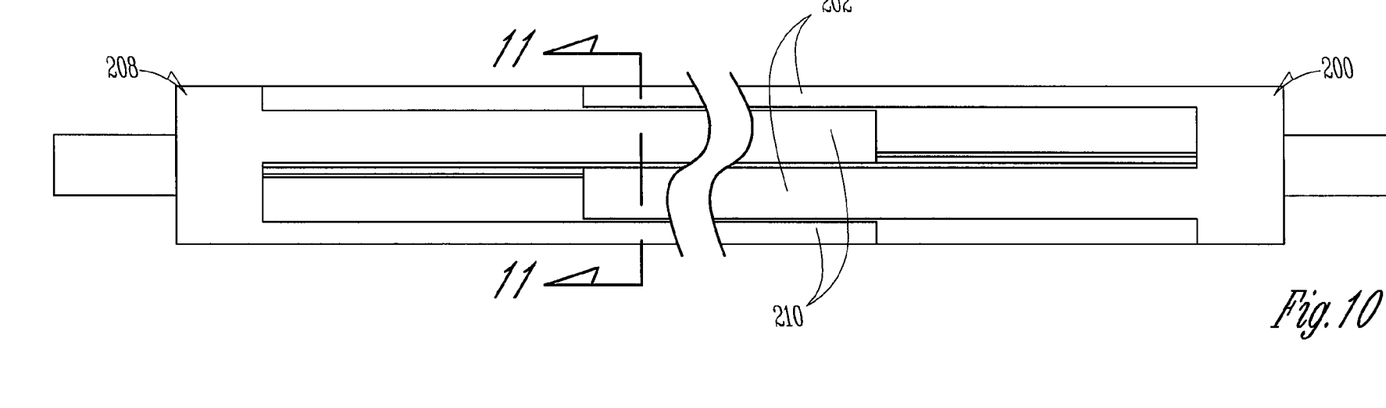
FIG. 10 is a side view illustrating tubular support members shown in FIG. 9.
Figure 11:
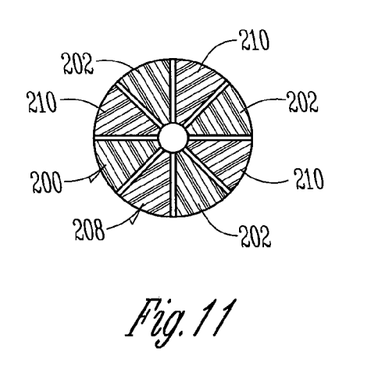
FIG. 11 is a cross-sectional view illustrating the tubular support members shown along line 11-11 in FIG. 10.

As shown in FIGS. 9 and 10, in one example, the first tubular support member 200 is telescopically coupled with a second tubular support member 208. The second tubular support member 208 has a complementary geometry to that of the first tubular support member 200. For example, the second tubular support member 208 presents fingers 210 that extend from a base 212 parallel to a longitudinal axis of the member 208. FIG. 11 shows fingers 202, 210 dimensioned and configured to slidably couple with each other and thereby allow telescoping movement between the first tubular support member 200 and the second tubular support member 208. In this example, the fingers 210 and base 212 of the second tubular support member 208 are dimensioned and configured to fit within the perimeter defined by the outer surfaces of the fingers 202 and base 204 of the first tubular support member 200 (described above). In one option, the second tubular support member 208 is coupled to the housing 150, disposed within the actuator lumen 122, and aligned along the longitudinal axis of the actuator lumen 122. As shown in FIG. 2, the proximal end of the second tubular support member 208 is disposed within actuator lumen 122 adjacent to the location actuator mechanism 130 assumes when pull wire 120 is fully compressed. The second tubular support member 208 extends from the proximal end to a distal end disposed where the actuator lumen 122 exits the catheter body 110 (described above). In one option, the first tubular support member 200 and second tubular support member 208 have a substantially similar outer perimeter. In another option, the first tubular support member 200 and second tubular support member 208 are dimensioned and configured to snugly couple with the surface defining the actuator lumen 122. The first tubular support member 200 and second tubular support member 208 are constructed from stainless steel, but may also be fabricated from other durable metals or plastics, including flexible materials.

Figure 15:
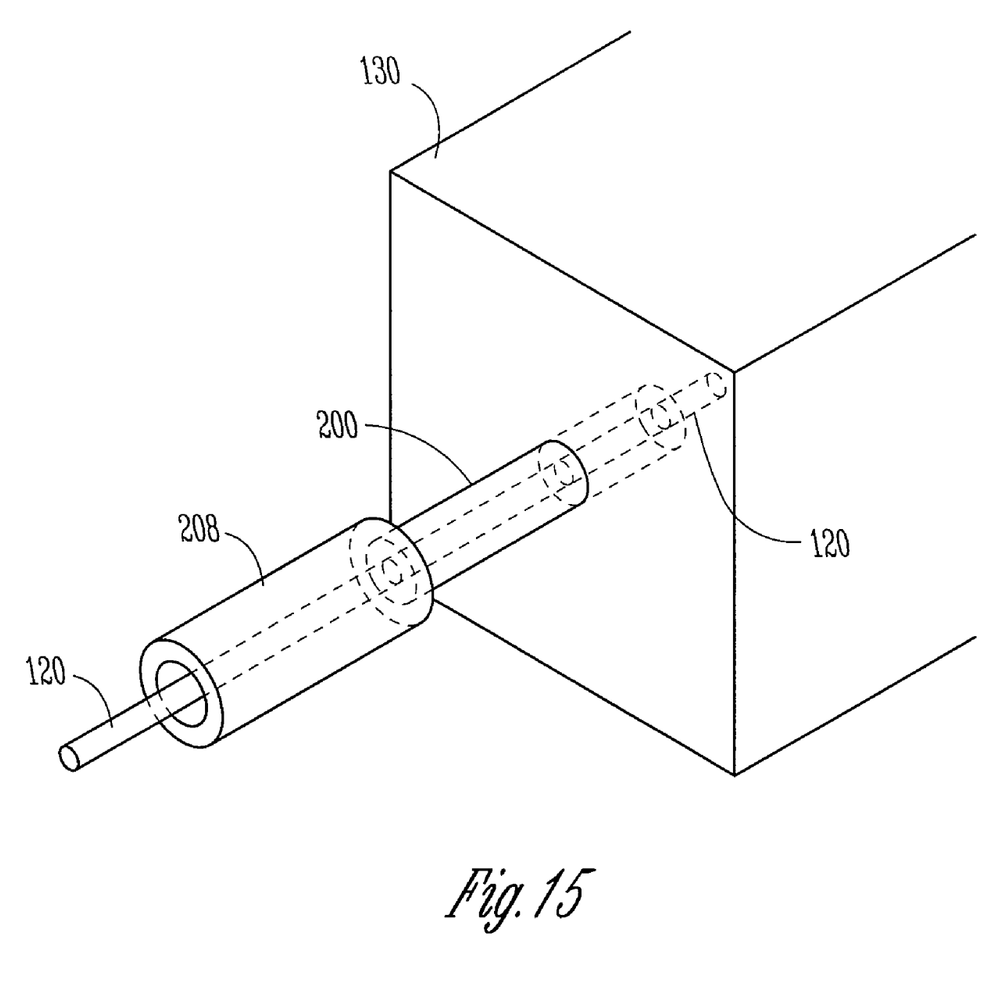
FIG. 15 is a perspective view illustrating tubular support members telescopically engaged in accordance with one embodiment.

Referring again to FIG. 9, a pull wire lumen 214 is provided in the second tubular support member 208. The pull wire lumen 214 is provided about the longitudinal axis of the second tubular support member 208, extends through the base 212 and is further defined by the inner surfaces of the fingers 210. As shown in FIG. 17, in one option, the pull wire 120 is received within the pull wire lumen 214 and is slidably coupled to the second tubular support member 208 therein. In one option, the pull wire 120 is slidably coupled to the inner surfaces of the fingers 210 and the base 212. The second tubular support member 208, in one option, is dimensioned and configured to restrain the pull wire 120 from moving laterally with respect to the longitudinal axis of the second tubular support member 208. As shown in FIG. 15, in another option, the second tubular support member 208 is a cylindrical member without fingers which has a complementary inner surface geometry to the outer surface of the first tubular support member 200, and is therefore slidably coupled with the first tubular support member 200 to allow slidable movement therebetween.

Figure 18:
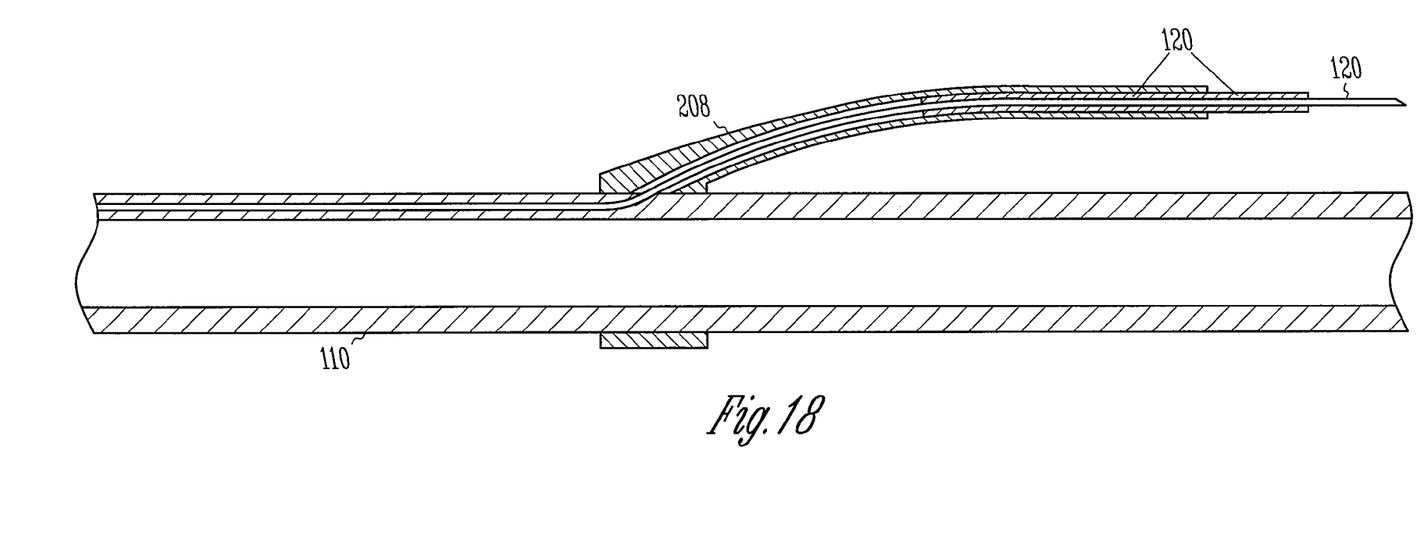
FIG. 18 is a cross-sectional view illustrating tubular support members telescopically engaged in accordance with one embodiment.

In still another option, as shown in FIG. 18, the second tubular support 208 is formed on the catheter body 110. In other words, the second tubular support member 208 is coupled to the catheter body 110 and extends from a distal end where pull wire 120 exits the catheter body to a proximal end. In one option, the second tubular support member 208 comprises at least a portion of the surface defining the actuator lumen 122. In another option, the outer surface of the second tubular support member 208 is coupled to the surface defining the actuator lumen 122. Optionally, the second tubular support member 208 is plastic and overmolded onto the catheter body 110. The second tubular support member 208 has a complementary inner surface geometry to the outer surface of the first tubular support member 200. The first tubular 200 is therefore slidably coupled with the second tubular support member 208 to allow slidable movement therebetween. In one example, the pull wire 120 is encapsulated with a sleeve including braided stainless steel impregnated with PTFE. In one option, the sleeve surrounds the first tubular member 200, but is not bonded to the first tubular support member or the pull wire 120. The second tubular support member 208 bonds with the sleeve when overmolded onto the catheter body 110. The sleeve prevents bonding of the second tubular support member 208 to the pull wire 120 and allows slidable movement between the first tubular support member 200 and second tubular support member.

In operation in one example, the first tubular support member 200 and second tubular support member 208 proximately abut the pull wire 120, but do not otherwise interfere with longitudinal movement of the pull wire 120. As best shown in FIG. 17, when the actuator 130 applies tension or compression to the pull wire 120 so as to deflect the catheter body 110, the first tubular support member 200 advances telescopically with respect to the second tubular support member 208 and actuator lumen 122 as it is fixedly coupled to the actuator mechanism 130. When the pull wire 120 is specifically compressed, which occurs when it is desired that the catheter body 110 be oriented oppositely from an orientation caused with tension, this abutment by the tubular support members 200, 208 braces the pull wire 120 and prevents it from buckling. Further, the telescoping movement of the first tubular support member 200 with respect to the second tubular support member 208 ensures that the compressed pull wire 120 is braced against buckling while the catheter body 110 is deflected to any degree.

As illustrated in FIG. 15, in another example, the cylindrical second tubular support member 208 slidably couples with, but does not interfere with the movement of the cylindrical first tubular support member 200 (as described above). In one option, the first tubular support member 200 is coupled to the pull wire 120 and fixedly coupled to the actuator mechanism 130, but does not interfere with longitudinal movement of the pull wire 120. When the actuator 130 applies tension or compression to the pull wire 120 so as to deflect the catheter body 110, the first tubular support member 200 moves telescopically with respect to the second tubular support member 208 as it is fixedly coupled to the actuator mechanism 130. When the pull wire 120 is specifically compressed, which occurs when it is desired that the catheter body 110 be oriented oppositely from an orientation caused with tension, the abutment by the first tubular support member 200 and the slidable coupling between the first tubular support member 200 and second tubular support member 208 braces the pull wire 120 and prevents it from buckling.

In yet another example, a first tubular support member 200 having a triangular or inverted 'Y' geometry within a complementary actuator lumen 122 is coupled to the pull wire 120 and is fixedly coupled to the actuator mechanism 130, but does not interfere with longitudinal movement of the pull wire 120. When the actuator 130 applies tension or compression to the pull wire 120 so as to deflect the catheter body 110, the first tubular support member 200 slidably moves within the actuator lumen 122 as it is fixedly coupled to the actuator mechanism 130. When the pull wire 120 is specifically compressed, which occurs when it is desired that the catheter body 110 be oriented oppositely from an orientation caused with tension, the first tubular support member 200 braces the pull wire 120 and prevents it from buckling.

In another embodiment, a method comprises manipulating a deflectable catheter assembly into a first orientation, the deflectable catheter assembly including a catheter body and housing attached to the catheter body, an actuator lumen extends therein. The housing is attached to the catheter body proximal end, and a flexible element extends from an actuator member within the housing through the actuator lumen to a deflectable distal end. A first tubular support member is coupled to the flexible element and fixedly coupled to the actuator member, and a second tubular support member is slidably coupled with the first tubular support member and slidably coupled to the flexible element. The first tubular support member and second tubular support member constrain lateral movement of the flexible element within the actuator lumen. In one option, the method includes longitudinally or telescopically advancing the flexible element and first tubular support member along the actuator lumen longitudinal axis. When the flexible element and first tubular support member are advanced, the second tubular support member is stationary with respect to the housing and the first tubular support member and second tubular support member remain aligned with the actuator lumen longitudinal axis. Additionally, the method includes further manipulating the actuator member to thereby actuate the flexible element and deflect the deflectable distal end into a disparate orientation. Furthermore, the method includes steering the deflectable catheter assembly which includes further manipulating the actuator member to deflect the deflectable distal end.

Several options for the method are as follows. For example, in one option, manipulating the actuator member to deflect the deflectable distal end into a disparate orientation includes constraining lateral movement of the flexible element within the actuator lumen with the first tubular support member and second tubular support member. In another option, further manipulating the actuator member to deflect the deflectable distal end into a disparate orientation includes longitudinally advancing the flexible element and first tubular support member along the actuator lumen longitudinal axis, while the second tubular support member is stationary with respect to the housing, and the first tubular support member and second tubular support member remain aligned with the actuator lumen longitudinal axis.

Advantageously, the above described deflectable catheter allows for bi-directional deflection of the catheter body using a single pull wire having a smaller diameter than what is otherwise required. The pull wire support assembly provides bracing for the narrow pull wire, when compressed, that prevents buckling due to articulation of the catheter into a disparate orientation from that caused by tensioning. Consequently, the pull wire and support assembly require significantly less volume within the catheter and leave additional space for the delivery lumen while allowing bi-directional deflection of the catheter.

Furthermore, the telescopic movement of one support member with respect to another allows bracing of the pull wire under any deflection of the catheter caused by compression. Consequently, any desired bi-directional deflection of the catheter is available where the support assembly is used with the narrow pull wire.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A deflectable catheter assembly comprising:
   a catheter body extending from a deflectable distal end to a proximal end and having an intermediate portion therebetween, wherein the catheter body includes an actuator lumen;
   a housing coupled to the proximal end of the catheter body;
   a flexible element extending from the housing through the actuator lumen to the deflectable distal end, wherein the deflectable distal end is controllable by pushing and pulling of the flexible element;
   a first tubular support engaged around the flexible element therein and coupled to an actuator mechanism disposed within the housing, the first tubular support movable with the actuator mechanism, wherein the first tubular support substantially constrains lateral movement of the flexible element; and
   a second tubular support telescopically engaged with the first tubular support.

2. The deflectable catheter assembly of claim 1, a second tubular support inner surface is dimensioned and configured to snugly envelop and slidably engage with the flexible element.

3. The deflectable catheter assembly of claim 2, a first tubular support outer surface has a complementary perimeter dimensioned and configured to slidably engage with a surface defining the actuator lumen.

4. The deflectable catheter assembly of claim 3, wherein the surface defining the actuator lumen has a circular geometry.

5. The deflectable catheter assembly of claim 3, wherein a first tubular support intermediate surface and a second tubular support intermediate surface are dimensioned and configured to slidably engage the first tubular support with the second tubular support.

6. The deflectable catheter assembly of claim 5, wherein the first tubular support intermediate surface, the first tubular support outer surface, and a first tubular support inner surface define at least one first tubular support finger.

7. The deflectable catheter assembly of claim 5, wherein the second tubular support intermediate surface, a second tubular support outer surface, and the second tubular support inner surface define at least one second tubular support finger.

8. The deflectable catheter assembly of claim 1, wherein the second tubular support inner surface is dimensioned and configured to snugly envelop and slidably engage with a first tubular support outer surface.

9. The deflectable catheter assembly of claim 1, wherein the first tubular support outer surface is dimensioned and configured to slidably engage with a surface defining the actuator lumen.

10. A deflectable catheter assembly comprising:
    a catheter body extending from a bi-directional deflectable distal end to a proximal end and having an intermediate portion therebetween, wherein the catheter body is bi-directionally deflectable and includes an actuator lumen;
    a housing attached to the proximal end of the catheter body;
    a flexible element extending from the housing through the actuator lumen to the bi-directional deflectable distal end, wherein the bi-directional deflectable distal end is controllable by at least one of pushing or pulling of the flexible element;
    a first tubular support engaged around the flexible element and coupled to an actuator mechanism disposed within the housing; and
    a second tubular support slidably engaged with the first tubular support.

11. The deflectable catheter assembly of claim 10, wherein the first tubular support and the second tubular support have a substantially similar outer perimeters.

12. The deflectable catheter assembly of claim 11, wherein a surface defining the actuator lumen is dimensioned and configured to snugly engage with the first tubular support and the second tubular support.

13. The deflectable catheter assembly of claim 12, wherein the first tubular support is slidably engaged with the surface defining the actuator lumen.

14. The deflectable catheter assembly of claim 12, wherein the second tubular support is coupled with the surface defining the actuator lumen.

15. The deflectable catheter assembly of claim 10, wherein an intermediate surface of the first tubular support and an intermediate surface of the second tubular support are dimensioned and configured to slidably engage the first tubular support with the second tubular support.

16. The deflectable catheter assembly of claim 15, wherein the first tubular support intermediate surface, a first tubular support outer surface, and a first tubular support inner surface define at least one first tubular support finger.

17. The deflectable catheter assembly of claim 15, wherein the second tubular support intermediate surface, a second tubular support outer surface, and a second tubular support inner surface define at least one second tubular support finger.

18. A deflectable catheter assembly comprising:
    a catheter body extending from a deflectable distal end to a proximal end and having an intermediate portion therebetween, wherein the catheter body includes an actuator lumen;
    a housing attached to the proximal end of the catheter body;
    a flexible element extending from the housing through the actuator lumen to the deflectable distal end, wherein the deflectable distal end is controllable by the flexible element; and
    means for constraining lateral movement of the flexible element within the actuator lumen, wherein the means for constraining is correspondingly movable with movement of the flexible element and is separate from the flexible element, the means including:

a first tubular support engaged around the flexible element and coupled to an actuator mechanism disposed within the housing, and
a second tubular support coupled to a surface defining the actuator lumen and slidably engaged with the first tubular support.

19. The deflectable catheter assembly of claim 18, wherein the first tubular support outer surface has an outer perimeter dimensioned and configured to snugly and slidingly reside within the surface defining the actuator lumen.

20. The deflectable catheter assembly of claim 18, wherein the first tubular support is slidably engaged with the surface defining the actuator lumen, and the second tubular support is slidably engaged with the first tubular support and slidably engaged with the flexible element.

21. A method comprising:
manipulating a deflectable catheter assembly into a first orientation, the catheter assembly including a catheter body and a housing coupled to a catheter body proximal end, an actuator lumen extending therein, a flexible element extending from an actuator member coupled with the housing through the actuator lumen to a deflectable distal end, a first tubular support engaged around the flexible element and coupled to the actuator member, and a second tubular support slidably engaged with the flexible element;
constraining lateral movement of the flexible element including bracing the flexible element with the first tubular support and the second tubular support; and
further manipulating the actuator member to thereby actuate the flexible element and deflect the deflectable distal end into a disparate orientation.

22. The method of claim 21, further comprising:
telescopically advancing the first tubular support with the actuator member with respect to the second tubular support.

23. The method of claim 21, wherein further manipulating the actuator member to deflect the deflectable distal end into the disparate orientation includes constraining lateral movement of the flexible element within the actuator lumen with the first tubular support telescopically engaged with the second tubular support.

24. A method comprising:
manipulating a deflectable catheter assembly into a first orientation, the catheter assembly including a catheter body and a housing coupled to a catheter body proximal end, an actuator lumen extending therein, a flexible element extending from an actuator member coupled with the housing through the actuator lumen to a deflectable distal end, a first tubular support engaged around the flexible element and coupled to the actuator member, and a second tubular support slidably engaged with the flexible element and slidably engaged with the first tubular support;
longitudinally advancing the flexible element and first tubular support along an actuator lumen longitudinal axis while the second tubular support is stationary with respect to the housing, and the first tubular support and second tubular support remain aligned with the actuator lumen longitudinal axis; and
further manipulating the actuator member to thereby advance the flexible element and deflect the deflectable distal end into a disparate orientation.

25. The method of claim 24, further comprising:
telescopically advancing the first tubular support with the actuator member with respect to the second tubular support.

26. The method of claim 24, further comprising:
constraining lateral movement of the flexible element including bracing the flexible element with the first tubular support and the second tubular support.

27. The method of claim 24, further manipulating the actuator member to deflect the deflectable distal end into the disparate orientation includes constraining lateral movement of the flexible element within the actuator lumen with the first tubular support and the second tubular support.

28. The method of claim 24, further manipulating the actuator member to deflect the deflectable distal end into the disparate orientation includes longitudinally advancing the flexible element and the first tubular support along the actuator lumen longitudinal axis while the second tubular support is stationary with respect to the housing, and the first tubular support and the second tubular support remain aligned with the actuator lumen longitudinal axis.

29. The deflectable catheter assembly of claim 1, wherein the catheter body includes an exit lumen in a catheter body sidewall, the exit lumen being in communication with the actuator lumen, and wherein the exit lumen is between the proximal end and the deflectable distal end, and the flexible element extends out of the catheter body through the exit lumen.

30. The deflectable catheter assembly of claim 10, wherein the catheter body includes an exit lumen in a catheter body sidewall, the exit lumen is between the proximal end and the bi-directional deflectable distal end, and wherein the second tubular support is coupled with the catheter body at the exit lumen with the flexible element extending out of the catheter body through the exit lumen and the second tubular support.

31. The method of claim 21, wherein constraining lateral movement of the flexible element includes bracing the flexible element with the second tubular support at an exit lumen in a catheter body sidewall, the exit lumen is between the proximal end and the deflectable distal end with the flexible element extending out of the catheter body through the exit lumen.

32. A deflectable catheter assembly, comprising:
a catheter body extending from a deflectable distal end to a proximal end and having an intermediate portion therebetween, wherein the catheter body includes an actuator lumen;
a housing coupled to the proximal end of the catheter body;
a flexible element extending from the housing through the actuator lumen to the deflectable distal end, wherein the deflectable distal end is controllable by pushing and pulling of the flexible element;
a first support comprising at least two spaced apart first support fingers disposed around the flexible element therein and coupled to an actuator mechanism disposed within the housing, the at least two spaced apart first support fingers being movable with the actuator mechanism; and
a second support coupled to a distal portion of the catheter body and comprising at least two spaced apart second support fingers disposed around the flexible element, wherein the at least two spaced apart first support fingers are telescopically engaged with the at least two spaced apart second support fingers in an alternating manner of a first support finger then a second support finger around the flexible element to substantially constrain lateral movement of the flexible element.

33. The deflectable catheter assembly of claim 32, wherein the first support comprises four spaced apart first support fingers and the second support comprises four spaced apart second support fingers telescopically engaged with the first support fingers.

34. The deflectable catheter assembly of claim 33, wherein the first and second support fingers each have a shape taken along a cross-section perpendicular to a longitudinal axis of the catheter body that tapers from a narrow portion immediately adjacent to the flexible element to a wider portion immediately adjacent to the actuator lumen.

35. The deflectable catheter assembly of claim 34, wherein the first and second support fingers each have a concave surface at their narrow portion immediately adjacent to the flexible element, and the first and second support fingers each have a convex surface at their wider portion immediately adjacent to the actuator lumen.

* * * * *